United States Patent [19]

Weissman

[11] 4,053,982
[45] Oct. 18, 1977

[54] DENTAL ANCHOR

[76] Inventor: Bernard Weissman, 225 E. 48th St., New York, N.Y. 10017

[21] Appl. No.: 669,688

[22] Filed: Mar. 23, 1976

[51] Int. Cl.² .............................................. A61K 5/02
[52] U.S. Cl. ............................................ 32/15; 85/61
[58] Field of Search ..................... 32/7, 15; 220/300; 85/61, 7, 8.6, 45, 9 R; 81/53 R, 53.2, 71, 73, 177 A, 57.31

[56] References Cited

U.S. PATENT DOCUMENTS

| 656,201 | 8/1900 | Meredith | 220/300 |
| 3,675,328 | 7/1972 | Weissman | 32/15 |

FOREIGN PATENT DOCUMENTS

| 867,643 | 5/1961 | United Kingdom | 85/61 |

Primary Examiner—Louis G. Mancene
Assistant Examiner—Mickey Yu
Attorney, Agent, or Firm—Friedman, Goodman & Teitelbaum

[57] ABSTRACT

A dental anchor is disclosed comprising an elongated member for anchoring a superstructure to a tooth. The elongated member includes at least one threaded section defining an anchoring portion that is attached to an L-shaped manipulating section by a reduced thickness portion in the form of an annular groove. The reduced thickness portion is frangible. The manipulating section is comprised of a cylindrical guide element that is coaxial with the anchoring portion and a torque transferring element having an axis that is substantially perpendicular to the axis of the guide element. The dental anchor is used with a dental attachment in the form of an elongated member having a first end that is adapted to be received by a power tool and a second end having a socket for receiving the manipulating section. Once the elongated dental anchor is inserted into a channel formed in the tooth, the manipulating section may be broken off at the frangible, reduced thickness portion without overstressing the tooth. Alternative embodiments provide second and third axially spaced apart reduced thickness portions, wherein the first reduced thickness frangible portion has a thickness greater than the thickness of the second frangible portion and, wherein the second reduced thickness frangible portion has a thickness greater than the third reduced thickness frangible portion. In the embodiments wherein multiple frangible portions are provided, each of the elongated anchoring portions are at least partially threaded and may be successively inserted into several channels formed in the tooth without reloading the dental tool.

5 Claims, 8 Drawing Figures

DENTAL ANCHOR

BACKGROUND OF THE DISCLOSURE

The present invention relates to dentistry in general and more particularly to an improvement in apparatus for building superstructure on broken or undermined dentition.

One form of anchoring a superstructure to the understructure of a tooth requires drilling a number of channels into the tooth or understructure. Depending upon the tooth involved, one or more anchoring rods are then inserted into the channels and are allowed to protrude above the understructure with the exposed or protruding portions of the rods serving as means for anchoring the superstructure. It should be noted that the rods that are used for this type of dental operation are extremely small and are, for example, on the order of 0.03 inches in diameter and approximately 0.2 inches in length. Because of the relatively small size of the rods and also because of the limited working areas, the rods are difficult to handle. When used with a dental power tool it is important that the rods be accurately guided and be prevented from relative axial movement with respect thereto. While there is prior art structure that can be used for the insertion of these rods into the channels in the tooth or understructure, it has been found that relative axial movement between the rod and dental tool was possible. In addition, it has also been found, with respect to the prior art, that the apparatus used for coupling the rod to the power driven dental tool permitted the rod to slip out of the coupling means because of the less than positive engagement between the coupling means and the rod.

SUMMARY OF THE INVENTION

Accordingly, it is an object of the present invention to provide improved means for building a superstructure on broken or undermined dentition.

Another object of the present invention is to provide improved means for positively holding the rods used for anchoring a superstructure to an understructure of a tooth.

A further object of the present invention is to provide improved means for assuring positive coupling between the powder driven tool and the rods used for anchoring a superstructure to the understructure of a tooth.

Still another object of the present invention is to provide anchoring means in the form of sections or rods that are interconnected to one another and yet are readily severable from one another without overstressing the tooth to thereby permit successive respective insertions into the understructure without the necessity for successively reloading the dental tool therefor.

Yet another object of the present invention is to provide improved means for coupling a power driven dental tool to the rods used for anchoring a superstructure to the understructure of the tooth whereby the coupling means positively rotates the rods in only a single angular direction.

Still another object of the present invention is to provide improved means for coupling a power driven dental tool to the rods used for anchoring a superstructure to the understructure of a tooth whereby axial movement of the rods relative to the coupling means is prohibited.

These objects are achieved in accordance with a preferred embodiment of the present invention, wherein the dental anchor comprises an elongated member and integral manipulating means therefor with the manipulating means having a portion that is non-concentrically integral with one end of the elongated member whereby the elongated member may be rotated by coupling means having one end thereof received in a power driven dental tool and the other end thereof in engagement with the manipulating means.

In order to prevent relative axial movement of the rods used for anchoring a superstructure to the understructure of the tooth, the coupling means is provided with an L-shaped slot at one end thereof with the L-shaped slot being formed through the wall of the coupling means. The manipulating means has a cooperatively associated L-shaped configuration with one section of the manipulating means being cylindrical and coaxial with the elongated member. The second section of the manipulating means has an axis that is substantially perpendicular to the axis of the cylindrical portion thereof. Intermediate the cylindrical portion of the manipulating means and the elongated member, there is provided a frangible, reduced thickness portion that is readily breakable once the rod has been inserted into the channel formed in the understructure of the tooth.

In an alternative embodiment of the present invention, the dental anchor is provided with two frangible, reduced thickness portions that are axially spaced apart. The frangible portion adjacent the manipulating means has a thickness that is greater than the thickness of the frangible portion remote from the manipulating means. In still another embodiment of the present invention, a third frangible, reduced thickness portion is provided which has a thickness that is less than either of the first two frangible, reduced thickness portions. In this last mentioned embodiment, the frangible reduced thickness portion closest to the manipulating means has the greatest thickness while the frangible reduced thickness portion most remote from the manipulating means has the smallest thickness. The intermediate frangible, reduced thickness portion has an intermediate thickness in the last mentioned embodiment.

A dental attachment in the form of coupling means is suitably secured to a power driven dental tool and the anchoring means is inserted in the coupling means by mating engagement of the L-shaped manipulating means integral with the anchoring means and the L-shaped slot at one end of the coupling means. The anchoring means is then rotated, through the coupling means, by the power driven dental tool so that the anchoring means is self-threaded axially into the channel formed in the understructure of the tooth without any relative axial movement between the anchoring means and the coupling means. When the elongated anchoring means has been sufficiently threaded into the channel in the understructure of the tooth, the threaded portion of the anchoring means most remote from the manipulating means may be snapped off without overstressing the tooth to thereby leave the threaded portion most proximate the manipulating means (in the embodiment where there are multiple threaded portions) intact with the manipulating means so that the threaded portion of the anchoring means that is still retained in the coupling means may be immediately inserted into a successive channel in the tooth without reloading the dental tool.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which like reference numerals designate like parts throughout the figures thereof and wherein.

DETAILED DESCRIPTION OF THE PREFERRED EMBODIMENT

Figure 1:
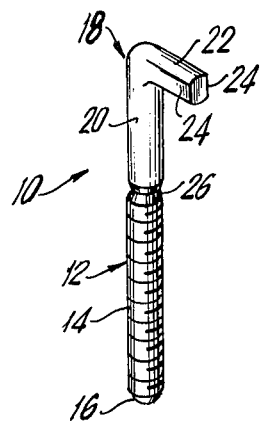
FIG. 1 is a perspective view illustrating one embodiment of the anchoring means comprising the present invention.

Referring now to the drawing, wherein like reference characters designate like or corresponding parts throughout the several views, there is shown in FIG. 1 a first embodiment of the anchoring means 10 comprising the present invention. The one-piece anchoring means 10 comprises an elongated body portion 12 having threads 14 formed on at least a portion thereof. The elongated body 12 terminates in a beveled or chamfered end 16. Manipulating means generally designated by the reference character 18 are formed integrally with the end of the elongated body 12 that is remote from the chamfered end 16.

The manipulating means 18 includes a cylindrical, first section defining guide means 20 which is concentrically integral with the end of the elongated body 12 that is remote from th chamfered end 16. The manipulating means 18 is further comprised of torque transferring means 22 that is integral with the guide means 20 and at a right angle thereto. The torque transferring means 22 includes at least two flatted side surfaces 24 which are opposed and substantially parallel to each other. For purposes to be described hereinafter, the manipulating means 18 is generally L-shaped and the dimension between the flatted surfaces 24 is less than the diameter of the cylindrical guide means 20.

Intermediate the elongated body 12 and the manipulating means 18 there is provided a frangible, reduced thickness portion 26. The thickness of the portion 26 is selected such that, when the threaded end 14 of the elongated body 12 is inserted in one of the channels formed in the understructure of the tooth or dentition, deflection of the manipulating means 18 will cause a rupture of the dental anchor 10 at the frangible, reduced thickness portion 26.

Figure 2:
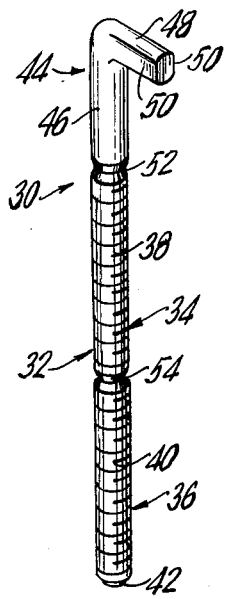
FIG. 2 is a perspective view illustrating an alternative embodiment of the anchoring means comprising the present invention.

FIG. 2 illustrates an alternative embodiment of a dental anchor 30 comprising the present invention. The one-piece dental anchor 30 includes an elongated body that is generally designated by the reference character 32 and which includes first and second coaxial sections 34 and 36. Threads 38 and 40 are formed on at least a portion of each of the sections 34 and 36, respectively, with the end of the section 36 terminating in a beveled or chamfered end 42. Manipulating means, generally designated by the reference character 44 are formed integrally with the end of the section 34 that is remote from the end 42 of the section 36. The manipulating means 44 includes a cylindrical guide means section 46 that is integral and coaxial with the elongated body 32 and a torque transferring means 48 that is integral with the guide means 46. It will be noted that the torque transferring means 48 has an axis that is substantially perpendicular to the axis of the cylindrical guide means 46. In addition, the torque transferring means 48 is provided with two opposed flatted surfaces 50 with the dimension between the surfaces 50 being less than the diameter of the cylindrical guide means 46.

A first frangible, reduced thickness portion 52 is formed intermediate the section 34 of the elongated body 32 and the guide means 46 and a second, frangible, reduced thickness portion 54 is formed intermediate the two sections 34 and 36 of the elongated body 32. The dimensions of the two frangible reduced thickness portion 52 and 54 are selected such that the thickness of the first frangible section 52 is greater than the thickness of the second frangible section 54. Thus, when the section 36 of the elongated body 32 is inserted into a channel formed in the understructure of the tooth or dentition and a deflecting force is applied to the dental anchor 30, the elongated body 32 will fracture first at the second frangible section 54. The second section 34 may then be inserted into a successive channel in the tooth or dentition without reloading the dental tool. When an angular deflecting force is once again applied to the manipulating means 44 of the dental anchor 30, fracture will occur at the frangible section 52.

Figure 3:
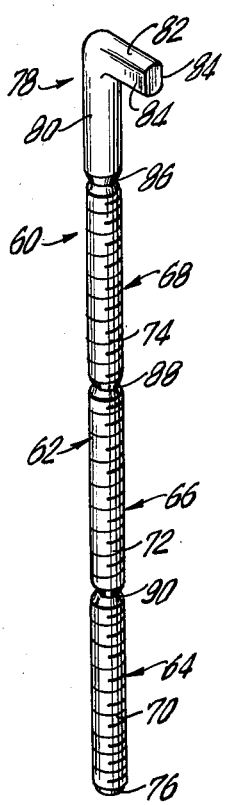
FIG. 3 is a perspective view illustrating still another embodiment of the anchoring means comprising the present invention.

Referring now to FIG. 3, there is shown still another embodiment of a dental anchor 60 comprising the present invention. The one-piece dental anchor 60 shown in FIG. 3 is provided with an elongated body portion generally designated by the reference character 62 which includes three coaxial sections 64, 66 and 68. At least a portion of each of the sections 64, 66 and 68 are provided with threads 70, 72 and 74 respectively. The section 64 terminates in a beveled or chamfered end 76. Manipulating means generally designated by the reference character 78 is formed integrally with the section 74 of the elongated body 62 and comprises a cylindrical guide means 80 and torque transferring means 82, the axis of which is perpendicular to the axis of the guide means 80. The torque transferring means 82 is also provided with two opposed flatted surfaces 84, the dimension between which is less than the diameter of the guide means 80.

A first frangible, reduced thickness portion 86 is forned intermediate the cylindrical guide means 80 and the adjacent end of the section 74 of the elongated body 62. A second frangible, reduced thickness portion 88 is formed intermediate the sections 74 and 72 of the elongated body 62 and a third frangible, reduced thickness portion 90 is formed intermediate the adjacent ends of the sections 72 and 70 of the elongated body 62. As in the previous embodiment, the thickness of the frangible portion 86 is greater than the thickness of the frangible portion 88, which, in turn, has a thickness greater than the frangible portion 90. It will be appreciated that the dental anchor 60 may be successively inserted into three different channels in the understructure of the tooth or dentition without reloading the dental tool since fracture will first occur at the frangible portion 90. Fracture will successively occur at the frangible portions 88 and 86 so that with the embodiment illustrated in FIG. 3, the dental tool need only be loaded once.

Figure 4:
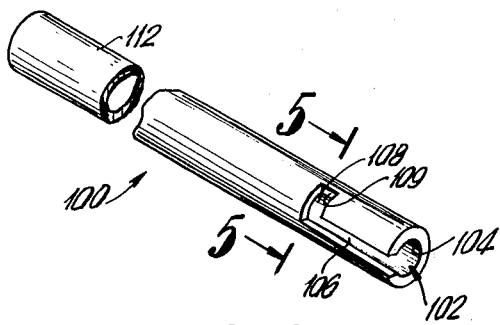
FIG. 4 is a fragmentary, perspective view illustrating the means for coupling the anchoring means comprising the present invention to a power driven dental tool.
Figure 5:
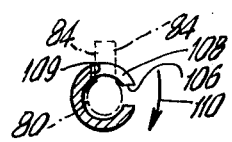
FIG. 5 is a transverse sectional view taken along line 5—5 of FIG. 4.

Any of the foregoing embodiments of the dental anchor comprising the present invention may be coupled to a motor driven dental tool by means of the structure shown in FIG. 4 and in FIG. 5. The coupling means 100 may be a tubular member or cylinder having an L-shaped socket 102 formed at one end thereof. The socket 102 is comprised of a cylindrical opening 104, a first axially extending slot 106 formed through the wall of the cylinder 100 and a second, partially circumferential slot 108 that starts at the end of the slot 106 that is remote from the end of the cylinder 100. The cylindrical opening 104 has a diameter that is approximately the same as and preferably only sightly greater than the diameter of any of the guide means 20, 46 or 80. The width of the slots 106 and 108 is slightly less than the diameter of the opening 104 and is approximately the same as or slightly greater than the dimension between the opposed, flatted surfaces 24, 50 and 84.

When any of the dental anchors 10, 30 or 60 are inserted in the coupling means 100, the guide means 20, 46 or 80 will be located in the cylindrical opening 104 of the socket 102 while the torque transferring means 22, 48 or 82 will have first moved through the slot 106 and will be positioned in the slot 108 as shown best in broken lines in FIG. 5. Rotation of the coupling means 100 in a clockwise direction as shown by the arrow 110 in FIG. 5 will cause one of the flatted surfaces 84 to bear against end wall 109 of the slot 108. This will, in turn, cause rotation of the dental anchor 60 and axial movement thereof into the channels formed in the understructure of the tooth or dentition. It should be appreciated at this time that the cooperation of the L-shaped manipulating means 18, 44 or 78 with the L-shaped slot 106, 108 of the coupling means 100 will effectively prevent any relative axial movement between the coupling means 100 and the dental anchor 10, 30 or 60 that is associated therewith. It should be further appreciated that by virtue of the aforementioned cooperation, the coupling means 100 and hence the dental tool (not shown) will not readily slip off the dental anchor 10, 30 or 60. Although a motor driven dental tool has not been illustrated, it should be understood that the end 112 of the coupling means 100 will be received in the chuck of the dental tool in a conventional manner.

Figure 6:
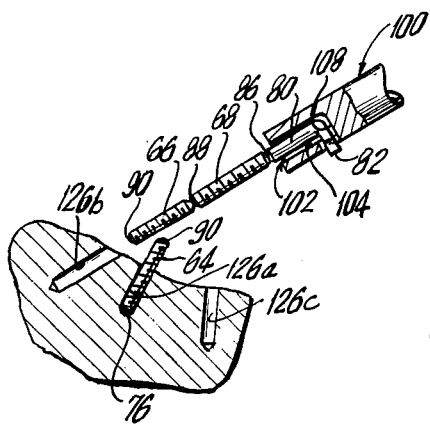
FIG. 6 is a cross sectional view of a tooth or dentition with its surface excavated prior to building of a superstructure thereon and with the first of three of the anchoring means comprising the present invention inserted therein.
Figure 7:
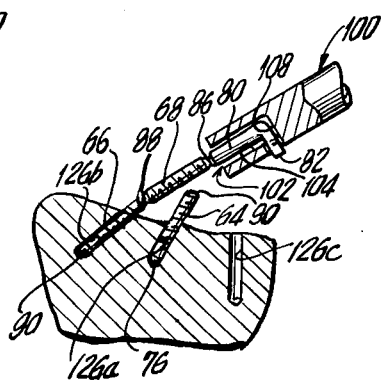
FIG. 7 is a view similar to FIG. 6 illustrating the excavated tooth or dentition with two of the three anchoring means comprising the present invention inserted therein.
Figure 8:
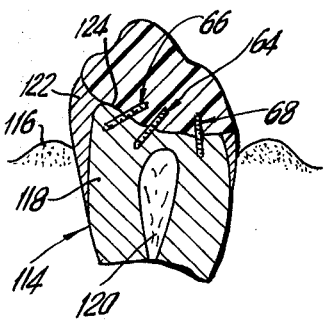
FIG. 8 is a view similar to FIG. 6 and FIG. 7 illustrating the projection of the anchoring means comprising the present invention into the built-up superstructure of the tooth or dentition.

Referring now to FIGS. 6, 7 and 8, and in particular to FIG. 8, there is shown a tooth or dentition 114 in the soft tissue or gingiva 116 of the human gum. As is well known to those skilled in the art, the body 118 of the tooth 114 is formed of dentin and encloses a pulp channel 120. The dentin projecting from the gingiva 116 is covered by a layer of enamel 122. In order to prepare the dentition for the building of a superstructure thereon, a portion of the enamel and a portion of the dentin are excavated to thereby remove decayed and undermined understructure and form an excavated surface 124 that is free of decay.

A plurality of channels 126a, b, c etc. are provided extending into the body 118 of the tooth 114 from the excavated surface 124. For this purpose a spiral drill (not shown) may be used in a conventional manner. A preferred diameter of the drill is, for example, 0.28 inches. The number of channels that are needed in a particular understructure will vary with the area of the surface 124 that is excavated as well as the portion of the dentin and enamel 122 that must be replaced by superstructure. While a single channel may be sufficient in some instances, it is more than likely that a plurality of channels will be necessary.

For purposes of illustrating a feature of the present invention, the dental anchor shown in FIG. 3 is utilized in the description of FIGS. 6, 7 and 8. It will be seen in FIG. 6 that the lower most section 64 of the elongated body 62 has already been threaded into the first channel 126a and has been broken off from the remainder of the elongated body 62 at the frangible portion 90, which has the smallest thickness. The section 66 of the elongated body 62 is in opposition to the channel 126b and is ready to be threaded therein. As shown in FIG. 7, the section 66 of the elongated body 62 has been broken away from the remainder of the elongated body 62 at the frangible portion 88 so that the final section 68 of the elongated body 62 may be threaded into the third and last channel 126c. Once this is accomplished, the manipulating means 78 may be broken off from the final section 68 of the elongated body 62 at the frangible portion 86. It will be appreciated that because of the construction described hereinabove, the dental anchor 60 need be loaded into the coupling means 100, and therefore into the power driven dental tool, only one time and yet three dental anchor sections 64, 66 and 68 may be threaded into the body 118 of the tooth 114. This feature of the present invention is made possible by the fact that the frangible portion 86 has the greatest thickness, the frangible portion 90 has the least thickness, while the frangible portion 88 has an intermediate thickness. The construction of the present invention described hereinabove, prevents overstressing of the tooth.

With each of the dental anchor sections 64, 66 and 68 fully threaded into their respective channels 126a, 126b and 126c, a small portion will project above the excavated surface 124. The superstructure may then be built up on the exposed excavated surface 124 in a conventional manner and as shown in FIG. 8.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental anchor for insertion into a channel in a tooth in combination with a dental attachment, said dental anchor comprising elongated anchoring means, manipulating means having a portion thereof that is non-concentrically integral with one end of said anchoring means for rotating said anchoring means about a longitudinal axis thereof and for moving said anchoring means axially into the channel of the tooth, at least a first frangible reduced thickness portion intermediate said anchoring means and said manipulating means, at least a portion of said anchoring means being threaded, said manipulating means being generally L-shaped and including an elongated guide means section immediately adjacent and integral at one end thereof with said anchoring means, said manipulating means further including an elongated torque transferring means section integral with an opposite end of said guide means section that is remote from said anchoring means, an axis of said torque transferring means section being substantially perpendicular to an axis of said guide means section, said guide means section being cylindrical and said torque transferring means section having at least two opposed flattened surfaces, a dimension between said flattened surfaces being less than a diameter of said cylindrical guide means section, said dental attachment comprising coupling means for operative association with a power tool, said coupling means including an elongated member having a first end that is adapted to be received by the power tool and a second end having a socket for operative association with said L-shaped manipulating means, said socket in said second end of said coupling means providing control means defined by an L-shaped slot extending through a wall of said socket, said slot comprising a first axially extending opening starting at said second end of said coupling means and a second partially circumferential opening contiguous with an opposite end of said first opening, a diameter of said socket being larger than a diameter of said guide means section, a width of said first and second openings of said slot being larger than said dimension between the two opposed flattened surfaces of said torque transferring means section, and said width of said first opening of said slot being smaller than said diameter of said guide means section so that said guide means section is prevented from passing through said first opening of said slot to hold said guide means section within said socket.

2. A combination as claimed in claim 1, wherein there is at least a second, frangible, reduced thickness portion formed on said anchoring means to thereby divide said anchoring means into two coaxial sections, said second frangible portion being at a location intermediate said first frangible portion and an end of said anchoring means that is remote from said manipulating means, said first frangible portion having a thickness greater than any thickness of said second frangible portion.

3. A combination as claimed in claim 2, wherein at least a portion of each of said two anchoring means sections is threaded.

4. A combination as claimed in claim 1, wherein there are at least second and third frangible, reduced thickness portions formed on said anchoring means to thereby divide said anchoring means into three sections, said second and said third frangible portions being in axially spaced apart relationship with respect to each other and with respect to said first frangible portion, said first frangible portion having a thickness greater than any thickness of said second frangible portion, said second frangible portion having a thickness greater than any thickness of said third frangible portion.

5. A combination as claimed in claim 4, wherein at least a portion of each of said three anchoring means sections is threaded.

* * * * *